United States Patent
Hoffrichter

(10) Patent No.: US 7,182,082 B2
(45) Date of Patent: Feb. 27, 2007

(54) RESPIRATORY THERAPY DEVICE FOR KEEPING FREE NATURAL RESPIRATORY TRACT OF A HUMAN BODY AND THE USE THEREOF IN ORDER TO PREVENT THE SOUND OF SNORING

(75) Inventor: Helmut Hoffrichter, Schwerin (DE)

(73) Assignee: Hoffrichter GmbH, Schwerin (DE)

( * ) Notice: Subject to any disclaimer, the term of this patent is extended or adjusted under 35 U.S.C. 154(b) by 0 days.

(21) Appl. No.: 10/483,634

(22) PCT Filed: Jul. 10, 2002

(86) PCT No.: PCT/DE02/02523

§ 371 (c)(1),
(2), (4) Date: Feb. 24, 2004

(87) PCT Pub. No.: WO03/006095

PCT Pub. Date: Jan. 23, 2003

(65) Prior Publication Data

US 2005/0098176 A1    May 12, 2005

(30) Foreign Application Priority Data

Jul. 12, 2001    (DE) ............... 201 11 396 U

(51) Int. Cl.
*A61M 16/00*    (2006.01)
*A61M 15/00*    (2006.01)
*A61H 31/00*    (2006.01)

(52) U.S. Cl. ............... 128/202.28; 128/200.24; 601/39; 601/41

(58) Field of Classification Search ........... 128/200.24, 128/202.28, 202.29, 203.11, 204.23, 204.18, 128/DIG. 23; 600/41, 43, 44; 602/18, 13; 601/39, 41–44
See application file for complete search history.

(56) References Cited

U.S. PATENT DOCUMENTS

| | | | | |
|---|---|---|---|---|
| 1,175,671 A | * | 3/1916 | Acklen ............... | 601/44 |
| 2,270,313 A | * | 1/1942 | Kraft ............... | 601/44 |
| 2,360,476 A | * | 10/1944 | Church ............... | 601/44 |
| 2,806,471 A | * | 9/1957 | Breese ............... | 602/17 |
| 2,825,327 A | * | 3/1958 | Tunnicliffe ............... | 601/44 |
| 2,832,335 A | * | 4/1958 | Huxley et al. ............... | 601/44 |
| 3,078,842 A | * | 2/1963 | Gray ............... | 601/44 |
| 3,285,244 A | * | 11/1966 | Cottrell ............... | 602/18 |
| 3,343,532 A | * | 9/1967 | Zumaglini ............... | 602/18 |
| 3,368,550 A | * | 2/1968 | Glascock ............... | 601/44 |
| 3,765,412 A | * | 10/1973 | Ommaya et al. ............... | 128/846 |

(Continued)

FOREIGN PATENT DOCUMENTS

| | | |
|---|---|---|
| DE | 3882126 | 6/1993 |
| EP | 0330740 | 9/1989 |
| WO | 9640335 | 12/1996 |

*Primary Examiner*—Teena Mitchell
(74) *Attorney, Agent, or Firm*—Horst M. Kasper

(57) ABSTRACT

In order to treat snoring and obstructive sleep apnea, the inner respiratory tract is subjected to atmospheric pressure and the outer surrounding area of the respiratory tract is subjected to artificial low-pressure, the difference between the inner atmospheric pressure and the outer low-pressure remaining constant. The respiratory therapy device consists of a pressure stable hollow body which surrounds the human body while keeping free the natural respiratory opening. Set hollow body forms the low-pressure chamber (7) is connected to a suction pump (3) by a suction tube (2). The invention method and respiratory therapy device make it possible to breathe in a free atmosphere.

20 Claims, 3 Drawing Sheets

U.S. PATENT DOCUMENTS

| | | | |
|---|---|---|---|
| 4,257,407 A | * | 3/1981 | Macchi ........................ 601/44 |
| 4,621,621 A | * | 11/1986 | Marsalis ...................... 601/44 |
| 4,930,498 A | * | 6/1990 | Hayek ......................... 601/44 |
| 4,982,735 A | * | 1/1991 | Yagata et al. .......... 128/204.23 |
| 5,076,259 A | * | 12/1991 | Hayek ......................... 601/44 |
| 5,101,808 A | * | 4/1992 | Kobayashi et al. ........... 601/44 |
| 5,402,535 A | * | 4/1995 | Green .......................... 2/468 |
| 5,403,266 A | * | 4/1995 | Bragg et al. ................... 602/5 |
| 5,655,522 A | | 8/1997 | Mechlenburg et al. |
| 5,752,927 A | * | 5/1998 | Rogachevsky ............... 602/18 |
| 5,947,115 A | | 9/1999 | Lordo et al. |

\* cited by examiner

RESPIRATORY THERAPY DEVICE FOR KEEPING FREE NATURAL RESPIRATORY TRACT OF A HUMAN BODY AND THE USE THEREOF IN ORDER TO PREVENT THE SOUND OF SNORING

(b) CROSS-REFERENCE TO RELATED APPLICATIONS

"Not Applicable"

(c) STATEMENT REGARDING FEDERALLY SPONSORED RESEARCH OR DEVELOPMENT

"Not Applicable"

(d) INCORPORATION-BY-REFERENCE OF MATERIAL SUBMITTED ON A COMPACT DISC (See 37 CFR 1.52(e)(5) and MPEP 608.05. Computer program listings (37 CFR 1.96(c)), "Sequence Listings" (37 CFR 1.821(c)), and tables having more than 50 pages of text are permitted to be submitted on compact discs.) or REFERENCE TO A "MICROFICHE APPENDIX" (See MPEP § 608.05(x). "Microfiche Appendices" were accepted by the Office until Mar. 1, 2001.)

"Not Applicable"

The Invention relates to a method according to the preamble of claim 1 and a respiratory therapy apparatus according to the preamble of claim 2. Such apparatus is employed for the treatment of the obstructive sleep apnoea. Another application is the prevention of snoring.

BACKGROUND OF THE INVENTION

Field of the Invention

So-called CPAP-apparatus (CPAP=Continuous Positive Airway Pressure) are known in respiratory therapy for generation of a positive respiratory passage pressure. These apparatuses make breathing air available in a face mask, wherein the pressure of the breathing air is continuously increased by several hPa relative to the atmospheric pressure. If a patient breathes in this artificial atmosphere, then the respiratory passages of the patient remain sufficiently wide opened for breathing based on the positive relative pressure. A CPAP-apparatus thus effects only a "pneumatic splinting" of the respiratory passages. The breathing process itself rests exclusively on own breathing.

Snoring is a suggestion of slackened and narrowed respiratory passages. In case of high flow speed through the throat, then the air pressure drops in the throat, since the distance between the air molecules becomes larger with increasing speed. As a consequence the slackened tissue collapses and deflates the air and completely blocks the air passage. The flow caused under pressure disappears thereby, the respiratory passages raise up and the air flows again until the air reaches a certain speed. This leads then immediately again to the next closure. The snoring sound is generated by a quick sequence of closure and opening of the respiratory passages. A CPAP-apparatus increases the air pressure relative to the atmospheric standard pressure (relative pressure) to such an extent that the flow induced pressure decrease cannot any longer effect a closure and the CPAP-apparatus thereby prevents the generation of the snoring sound.

If the mechanism forming the base of the snoring surpasses a certain degree of intensity, then the breathing drive operation is interrupted. Now a treatment requiring disease of "obstructive sleep apnoea" is present, which concerns at least one percent of the population. The disease of "obstructive sleep apnoea" is treated predominantly with CPAP-apparatuses. Mechanical auxiliary agents or operative surgical procedures are further, but subordinated possibilities of therapy.

A disadvantage of known CPAP-apparatus comprises that they have an internal flow resistance, where the patient has to overcome the internal flow resistance with his or her breathing muscles. This results in an additional load, since the internal resistance of the apparatus is added to the respiratory passage resistance of the patient.

A further disadvantage comprises that the air is warmed up during passage through the apparatus and thereby the relative humidity of the air is decreased. As a consequence the air withdraws water from the mucuous membranes and linings. Since dried mucuous membranes and linings not only are unpleasant, but in addition lose their protective function, an air humidification is required in connection with the breathing therapy. Therefore, CPAP-apparatuses are equipped with an integrated air humidifier or an air humidifier is placed between the CPAP-apparatus and the patient as an additional apparatus. Additional disadvantages of CPAP-apparatuses are operational noises, hindrance by the facemask, hygienic risks and high energy usage.

Therefore it is an object of the present Invention to furnish a method of the recited kind and a corresponding breathing therapy apparatus, which enables a breathing at the free atmosphere. Further tasks are the elimination of the facemask, the reduction of the operating noise, the improvement of the hygiene and the reduction of the energy usage.

This object is achieved on the side of the method by the characterizing features of claim 1 and on the apparatus side by the characterizing features of claim 2. Advantageous possibilities of embodiments of the breathing therapy apparatus result from the sub claims 3 to 6.

The Invention eliminates the disadvantages of the state-of-the-art.

The collapsing and deflating of the respiratory passages in the throat region is prevented by bringing the complete body or preferably only parts of the body, for example of the front soft neck region into a chamber subject to reduced relative pressure, since then the high static pressure of the standard atmosphere splints the respiratory passages. This method presents in a physical sense a reversal of the CPAP-principle known according to the state-of-the-art. The patient can therewith breathe at standard atmosphere and the Invention method has the advantage that the hindering breathing mask is not any longer required.

Since the breathing air does not have to flow through any technical device components, there is also no additional breathing resistance present and the breathing muscles are not charged in addition. No additional breathing air humidification is required based on the breathing at standard atmosphere and the expenditure for an air humidifier is dispensed with.

Since the breathing therapy apparatus according to the present Invention does not any longer have to deliver the breathing air, but only still has to maintain the negative relative pressure in the chamber, the breathing hose is also dispensed with in favor of a thin suction hose. The suction blower does not have to move however large air volumes, but always only that volume which flows in based on leakages in the under pressure chamber. The required power of the suction blower is therewith small and can also be furnished by a battery. In addition, the complete blower can be kept fairly small, whereby a good sound insulation becomes possible.

Advantages also result in the safety region. A failure of the blower does not automatically result in a carbon dioxide (CO2)-back breathing. The symptoms of the obstructive sleep apnoea would again be present in such a case, however more could not happen. Hygienic advantages are generated, since no auxiliary parts such as hose and mask are flowed through by the breathing air and since therewith no further condensation water can be formed. The timed cleaning cycle can therefore be substantially increased. The use of the apparatus by different patients is of no concern.

Since the apparatus is simply constructed and cost favorably produceable and since no dangers are associated with the application of the apparatus, the apparatus can be employed also without a doctor's prescription, for example in order to prevent snoring. Known devices for preventing of snoring comprise mostly an object, which has to be carried in the mouth or at the teeth. Accidents can be generated easily therewith, for example where the employed anti-snoring clasp disengages and is swallowed.

The Invention is to be illustrated in more detail in the following in connection with an application embodiment example. The associated figure shows the construction of a simple possibility of realization.

BRIEF DESCRIPTION OF THE SEVERAL VIEWS OF THE DRAWING(S)

There is shown in:

Figure 1:
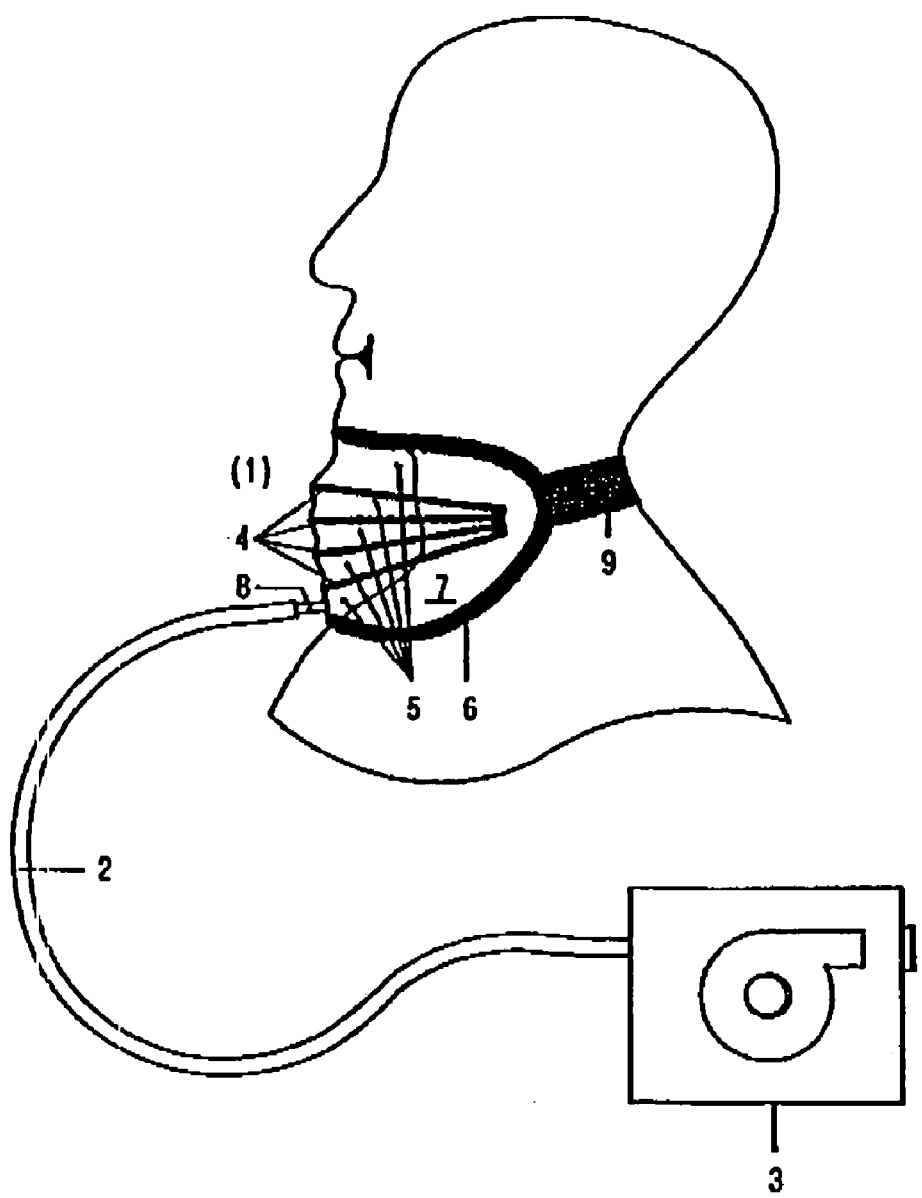
FIG. 1 is a view of a schematic diagram of the present invention.
Figure 2:
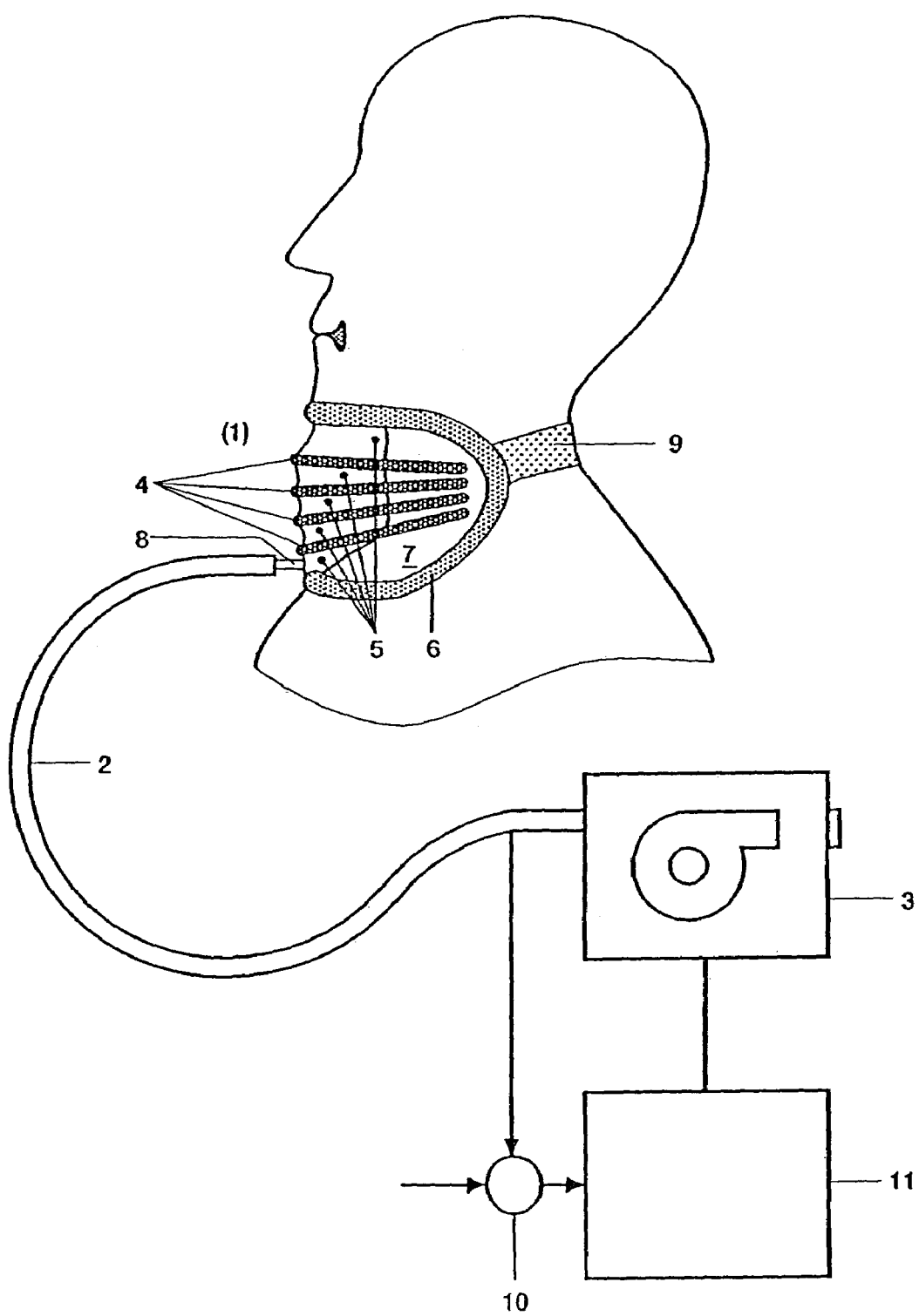
FIG. 2 is a view of a schematic diagram of the present invention with electronic pressure control device.
Figure 3:
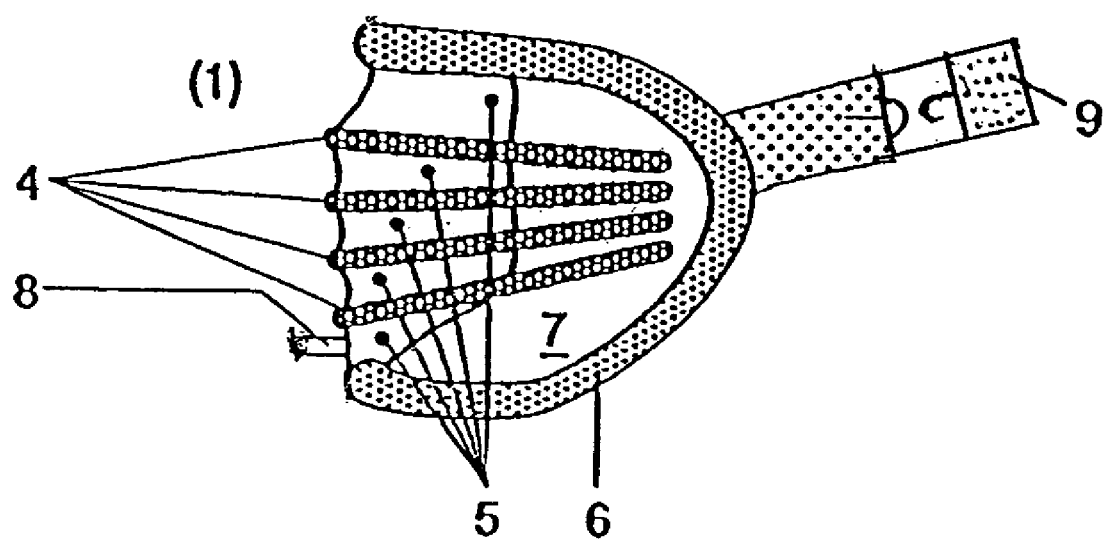
FIG. 3 is a view of a schematic diagram showing a hook and loop closure on a nape band.

The example device comprises a neck mask 1, a suction hose 2 and a suction pump 3. The neck mask 1 is a half opened chamber, wherein the chamber dome shaped spans over the front (ventral) neck region. The edge of the neck mask 1 surrounds in a circulation the region starting from the chin at the two sides of the lower jaw along to the sides of the neck and from there again toward the front at the bottom area to the upper end of the breast bone (sfernura). The sealing device 6 is disposed along the circulation, wherein the sealing device 6 rests on the skin in a used state. The open side of the neck mask 1 is closed by the skin of the patient in this manner and a closed chamber volume 7 is formed.

The surface of the neck mask is furnished such is that the surface is stiff perpendicular to this surface, however flexible in the extension direction of the surface. The mask surface can therewith be increased and be decreased during nodding motions of the head and the mask surface can be pulled sideways during rotary motions of the head. This property is achieved in the example by having the envelope of the neck mask 1 made out of an elastic skin 5, for example out of rubber or another elastomer over an under construction out of a stabilizing skeleton brace or framework clasp 4.

A connection pipe shaped air discharge 8 is disposed a suitable location, preferably in the lower region of the neck mask 1, wherein the air discharge 8 leads from the outside through the envelope of the neck mask 1 into the closed chamber volume 7 and the wherein the air discharge 8 is connected to the suction side of the suction pump 3 through the suction hose 2. A nape band 9 is furnished for application and for stabilization of the correct seating of the neck mask 1, wherein the nape band 9 would be furnished with a closure, preferably with a hook and loop closure.

A method is disclosed for maintaining the upper respiratory passages of the human opened through a compressed air rail.

The suction pump 3 generates a constant under pressure of a few hPa in the closed chamber volume 7 through the suction hose 2 connected to the air discharge 8 during the operation. This is accomplished by a pressure automatic controlled suction pump or by setting a certain rotary speed at a suction blower. In case leakages occur between the skin of the patient and the sealing device , then the leakage volume streaming into the closed chamber volume 7 is suctioned off. Also head motions do not effect any change of the under pressure in the closed chamber volume 7, wherein the suction pump 3 or the employed suction blower exhibit a device 11 for automatic pressure control. A pressure difference point 10 is disposed between the under pressure present in the suction hose 2 and the preset suction pressure $P_{set}$.

The respiratory passage is subjected to the pressure of the atmosphere and the extra corporal region of the respiratory passage of the neck is subjected to an artificial under pressure, wherein the difference between the inner atmospheric pressure and the outer under pressure is maintained constant.

Since the neck mask 1 spans over the complete ventral neck region and furnishes an artificial under pressure atmosphere at this location with the closed chamber volume 7, the respiratory passages of the patient are splinted by the pressure of the standard atmosphere. Flow caused pressure decreases in the throat region of the patient do not any longer lead to a collapse and deflation of the respiratory passages. Snoring sounds cannot any longer be generated. Patients with an obstructive sleep apnea can breathe freely and have again a sound sleep.

LIST OF REFERENCE CHARACTERS EMPLOYED 1 pressure stable cap
2 suction hose
3 suction pump
4 skeleton braces
5 surface of the chamber
6 sealing device
7 under pressure chamber
8 air discharge
9 nape band

The invention claimed is:

1. A method for maintaining the upper respiratory passages of a human opened through a compressed air rail, characterized in that the upper respiratory passage is subjected to a pressure of an atmosphere, wherein a neck mask is furnished, wherein the neck mask is placed over a front area of the neck of a user, and wherein an extra corporal region of the upper respiratory passage of a neck is subjected to an artificial under pressure, wherein a difference between an inner atmospheric pressure and the outer artificial under pressure is maintained constant.

2. A breathing therapy apparatus characterized by a pressure stable hollow body, wherein the hollow body is adapted to surround a front side of a neck of a human body while leaving a natural breathing opening free and unimpeded and wherein the pressure stable hollow body is adapted to form an under pressure chamber (7) at least in an extra corporal region of a respiratory passage, wherein the under pressure chamber (7) is connected to a suction pump (3) through a suction hose (2).

3. A breathing therapy apparatus characterized
by a pressure stable hollow body, wherein the hollow body is adapted to surround the human body while leaving the natural breathing opening free and unimpeded and wherein the pressure stable hollow body is adapted to form an under pressure chamber (7) at least in the extra corporal region of the respiratory passage, wherein under pressure chamber (7) is connected to a suction pump (3) through a suction hose (2), wherein
the pressure stable hollow body is formed as a cap (1), wherein the cap has an edge and which edge is adapted to surround the front neck region starting from the chin at the two sides of the lower jaw, the sides of the neck and the area of the collar bone along up the upper end of the breast bone and is formed such that the cap is adapted to cover the skin region bordered by the edge of the cap in a dome shape and with a distance to the skin.

4. The breathing therapy apparatus according to claim 3, characterized in that the pressure stable hollow body cap (1) is made of a material, which is pressure stable in a direction perpendicular to a body surface and is such flexible in surface direction that motions of the head are permissible.

5. The breathing therapy apparatus according to claim 4, characterized in that the pressure stable hollow body cap (1) comprises an integrated base construction out of stabilizing skeleton braces (4) and an elastic skin 5 disposed above the skeleton braces (4), wherein the elastic skin comprises rubber or another elastomer.

6. The breathing therapy apparatus according to claim 2, characterized in that the suction pump (3) is equipped with a pressure automatic control device for generating and maintaining a pre-settable under pressure.

7. A breathing therapy apparatus comprising
a pressure stable hollow body adapted to surround a front side of a neck of a human body while maintaining a natural breathing opening of the human body free and wherein the pressure stable hollow body is adapted to form an under pressure chamber (7) at the front side of the neck of the human body;
a suction hose having a first end connected to the pressure stable body from an outside and having a second end;
a suction pump (3) connected to the second end of the suction hose (2),
wherein the under pressure chamber (7) is connected to the suction pump (3) through the suction hose (2).

8. The breathing therapy apparatus according to claim 7, wherein
the pressure stable hollow body is formed as a cap (1), wherein the cap is adapted to surround with an edge a front neck region starting from a chin at two sides of a lower jaw, sides of the neck and an area of a collar bone along up an upper end of a breast bone and is formed such that the cap is adapted to cover a skin region bordered by the edge of the cap in a dome shape and with a distance to the skin.

9. The breathing therapy apparatus according to claim 8, wherein the pressure stable hollow body cap (1) is made of a material, which is pressure stable in a direction perpendicular to a body surface and is such flexible in surface direction that motions of a head are permissible.

10. The breathing therapy apparatus according to claim 8, wherein the pressure stable hollow body cap (1) comprises an integrated base construction out of stabilizing skeleton braces (4) and an elastic skin 5 disposed above the skeleton braces (4), wherein the elastic skin comprises rubber or another elastomer.

11. The breathing therapy apparatus according to claim 7 further comprising
a pressure automatic control device (11) for generating and maintaining a pre-settable under pressure, and connected to the suction pump (3).

12. The breathing therapy apparatus according to claim 7 wherein the pressure stable hollow body forms a neck mask adapted to span over the complete ventral neck region of a user and to furnish an artificial under pressure.

13. The breathing therapy apparatus according to claim 7 wherein the under pressure chamber is dome shaped and spans over the front side of the neck of the human body and further comprising
a sealing device disposed along an edge of the pressure stable hollow body and adapted to rest on a skin of a user.

14. The breathing therapy apparatus according to claim 7 wherein
wherein an edge of the pressure stable hollow body is adapted to surround starting from a chin, two sides of the lower jaw along to the sides of the neck and from there again toward the front at a bottom area to an upper end of a breast bone of a user.

15. The breathing therapy apparatus according to claim 7 wherein a surface of the pressure stable hollow body is furnished stiffly resisting to a force applied perpendicular to this surface and flexibly yielding to a force applied in an extension direction of the surface.

16. The breathing therapy apparatus according to claim 7 further comprising
a connection pipe shaped air discharge (8) disposed in a lower region of the pressure stable hollow body, wherein the connection pipe shaped air discharge (8) leads from outside through an envelope of the pressure stable hollow body into the under pressure chamber (7) and wherein the connection pipe shaped air discharge (8)is connected to a suction side of the suction pump (3).

17. The breathing therapy apparatus according to claim 7 further comprising
a nape band (9) attached to the pressure stable hollow body, and
wherein the nape band includes a hook and loop closure.

18. A method for maintaining the upper respiratory passages of a human opened comprising
subjecting the upper respiratory passage to an atmospheric pressure;
furnishing a neck mask having an edge;
placing the neck mask over the front area of the neck of a user;
subjecting an extra corporal region of the upper respiratory passage in a front area of a neck to an artificial under pressure; and
maintaining a difference between the atmospheric pressure and the artificial under pressure at a constant value.

19. The method according to claim 18 further comprising
sealing a chamber formed between neck mask and skin of the user with a sealing device disposed along the edge of the neck mask;
connecting a suction hose to the chamber;
connecting a suction pump to the suction hose;
setting a certain rotary speed at the suction pump increasing a surface of the neck mask during a nodding motion of a head;
decreasing the surface of the neck mask during a nodding motion of the head.

20. The method according to claim 19 further comprising
attaching the neck mask with a nape band around the neck of the user;
employing a device for automatic pressure control in the chamber.

* * * * *